United States Patent
Gottemukkula

(10) Patent No.: US 10,956,704 B2
(45) Date of Patent: Mar. 23, 2021

(54) NEURAL NETWORKS FOR BIOMETRIC RECOGNITION

(71) Applicant: Advanced New Technologies Co., Ltd., George Town (KY)

(72) Inventor: Vikas Gottemukkula, Kansas City, KS (US)

(73) Assignee: Advanced New Technologies Co., Ltd., Grand Cayman (KY)

(*) Notice: Subject to any disclaimer, the term of this patent is extended or adjusted under 35 U.S.C. 154(b) by 12 days.

(21) Appl. No.: 16/183,274

(22) Filed: Nov. 7, 2018

(65) Prior Publication Data

US 2020/0143137 A1   May 7, 2020

(51) Int. Cl.
| | |
|---|---|
| *G06K 9/00* | (2006.01) |
| *G06N 3/08* | (2006.01) |
| *A61B 5/1171* | (2016.01) |
| *G06N 3/04* | (2006.01) |
| *G06F 21/32* | (2013.01) |

(52) U.S. Cl.
CPC ........ *G06K 9/00026* (2013.01); *A61B 5/1171* (2016.02); *G06K 9/00885* (2013.01); *G06N 3/04* (2013.01); *G06N 3/08* (2013.01); *G06F 21/32* (2013.01); *G06K 2009/00939* (2013.01)

(58) Field of Classification Search
CPC ............ G06K 9/00026; G06K 9/00885; A61B 5/1171; G06N 3/04; G06N 3/08
See application file for complete search history.

(56) References Cited

U.S. PATENT DOCUMENTS

| | | | | |
|---|---|---|---|---|
| 2018/0129937 A1* | 5/2018 | Bradbury | ............. | G06N 3/0445 |
| 2018/0218256 A1* | 8/2018 | Raviv | .................. | G06N 3/0454 |
| 2018/0373979 A1* | 12/2018 | Wang | ................. | G06K 9/00671 |

OTHER PUBLICATIONS

Schroff, "FaceNet: a unified embedding for face recognition and clustering", IEEE, 2015.*
Schroff et al. "FaceNet: A Unified Embedding for Face Recognition and Clustering" arXiv:1503.03832v3 [cs.CV]; Jun. 17, 2015; 10 pages.

* cited by examiner

*Primary Examiner* — Ruiping Li
(74) *Attorney, Agent, or Firm* — Fish & Richardson P.C.

(57) ABSTRACT

Methods, systems, and apparatus, including computer programs encoded on a computer storage medium, for training an encoder neural network having multiple encoder neural network parameters. The encoder neural network is configured to process a biometric data sample in accordance with current values of encoder neural network parameters to generate as output an embedded representation of the biometric data sample. The embedded representation includes: (i) an inter-class embedded representation, and (ii) an intra-class embedded representation that is different than the inter-class embedded representation.

20 Claims, 6 Drawing Sheets

NEURAL NETWORKS FOR BIOMETRIC RECOGNITION

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that performs neural network training.

According to a first aspect there is provided a method for training an encoder neural network having multiple encoder neural network parameters. The encoder neural network is configured to process a biometric data sample in accordance with current values of encoder neural network parameters to generate as output an embedded representation of the biometric data sample. The embedded representation includes: (i) an inter-class embedded representation, and (ii) an intra-class embedded representation that is different than the inter-class embedded representation.

The method includes obtaining a positive biometric data sample characterizing an identity of a first person and a negative biometric data sample characterizing an identity of a second person. The identity of the first person is different than the identity of the second person. The positive biometric data sample and the negative biometric data sample are processed using the encoder neural network and in accordance with the current values of the encoder neural network parameters to generate an embedded representation of the positive biometric data sample and an embedded representation of the negative biometric sample. A gradient of a loss function with respect to the encoder neural network parameters is determined. The loss function includes a first term that encourage the inter-class embedded representation of the positive biometric data sample and the inter-class embedded representation of the negative biometric data sample to be less similar than the embedded representation of the positive biometric data sample and the embedded representation of the negative biometric data sample. The current values of the encoder neural network parameters are adjusted using the gradient of the loss function.

In some implementations, the training further includes obtaining an additional positive biometric data sample characterizing the identity of the first person. The additional positive biometric data sample is processed using the encoder neural network and in accordance with the current values of the encoder neural network parameters to generate an embedded representation of the additional positive biometric data sample. The loss function includes a second term that encourage the inter-class embedded representation of the additional positive biometric data sample and the inter-class embedded representation of the positive biometric data sample to be more similar than the embedded representation of the additional positive biometric data sample and the embedded representation of the positive biometric data sample.

In some implementations, the method further includes jointly training the encoder neural network and a decoder neural network. The decoder neural network has multiple decoder neural network parameters and is configured to process an embedded representation of a biometric data sample in accordance with current values of decoder neural network parameters to generate as output a reconstruction of the biometric data sample. The joint training includes processing the embedded representation of the positive biometric data sample and the embedded representation of the negative biometric data sample using the decoder neural network and in accordance with the current values of the decoder neural network parameters to generate a reconstruction of the positive biometric data sample and a reconstruction of the negative biometric data sample. A gradient of the loss function with respect to the decoder neural network parameters is determined. The loss function includes one or more third terms that encourage the positive biometric data sample and the reconstruction of the positive biometric data sample to be more similar and that encourage the negative biometric data sample and the reconstruction of the negative biometric data sample to be more similar. The current values of the decoder neural network parameters are adjusted using the gradient of the loss function.

In some implementations, the method further includes determining a generic embedded representation from the embedded representation of the positive biometric data sample. The generic embedded representation is processed using the decoder neural network and in accordance with the current values of the decoder neural network parameters to generate a generic reconstruction. The generic reconstruction is processed using the encoder neural network and in accordance with the current values of the encoder neural network parameters to generate an embedded representation of the generic reconstruction. The loss function includes one or more fourth terms that encourage the inter-class embedded representation of the generic reconstruction and the inter-class embedded representation of the negative biometric data sample to be less similar and that encourage the inter-class embedded representation of the generic reconstruction and the inter-class embedded representation of the positive biometric data sample to be more similar.

In some implementations, determining a generic embedded representation includes determining an inter-class embedded representation included in the generic embedded representation by averaging the inter-class embedded representation of the positive biometric data sample and inter-class embedded representations of one or more additional positive biometric data samples.

In some implementations, determining a generic embedded representation includes determining an intra-class embedded representation included in the generic embedded representation to be a predetermined intra-class embedded representation where each component of the intra-class representation has a same value.

In some implementations, each biometric data sample is an image depicting an eye of a person who is a source of the biometric data sample.

In some implementations, the encoder neural network is a convolutional neural network.

In some implementations, similarity is measured based on a cosine similarity measure.

According to a second aspect there is provided a system including a data processing apparatus and a memory in data communication with the data processing apparatus and storing instructions that cause the data processing apparatus to train an encoder neural network using the operations of the previously described method.

According to a third aspect there is provided one or more non-transitory computer storage media storing instructions that when executed by one or more computers cause the one or more computers to train an encoder neural network using the operations of the previously described method.

Particular embodiments of the subject matter described in this specification can be implemented so as to realize one or more of the following advantages.

Authentication systems identify users who are authorized to, for example, access secure locations (e.g., physical locations or logical data storage areas) or allowed to perform actions (e.g., transferring funds). To operate effectively, authentication systems must accurately identify authorized users. The training system described in this specification can train an encoder neural network for use in an authentication system. An encoder neural network trained by the training system described in this specification can be used to enable an authentication system to authenticate users more effectively. That is, an encoder neural network trained by the training system described in this specification can enable an authentication system to generate fewer false positives, fewer false negatives, or both, than an authentication system using a conventional encoder neural network. A false positive refers to an unauthorized user being incorrectly identified as an authorized user, and a false negative refers to an authorized user being incorrectly identified as an unauthorized user.

More specifically, an encoder neural network trained by the training system described in this specification is configured to generate embedded representations of biometric data samples that include an inter-class embedded representation and an intra-class embedded representation. The inter-class embedded representation can be understood to characterize features of biometric data samples which are potentially invariant across different biometric data samples from the same person. The intra-class embedded representation can be understood to characterize features of biometric data samples which are potentially variable between biometric data samples from the same person. For example, if a biometric data sample is an image of a face, the inter-class embedded representation may implicitly characterize underlying structural features of the face, while the intra-class embedded representation may implicitly characterize the presence of glasses or an expression or facial hair on the face. The inter-class embedded representations of biometric data samples generated by an encoder neural network as described in this specification can be used to generate enrollment templates which characterize the identities of people more discriminatively than enrollment templates generated using conventional encoder neural networks.

The training system described in this specification can train an encoder network over fewer training iterations, using fewer training examples, or both than some conventional training systems. Therefore, the training system described in this specification may consume fewer computational resources (e.g., memory, computing power, or both) than some conventional training systems.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
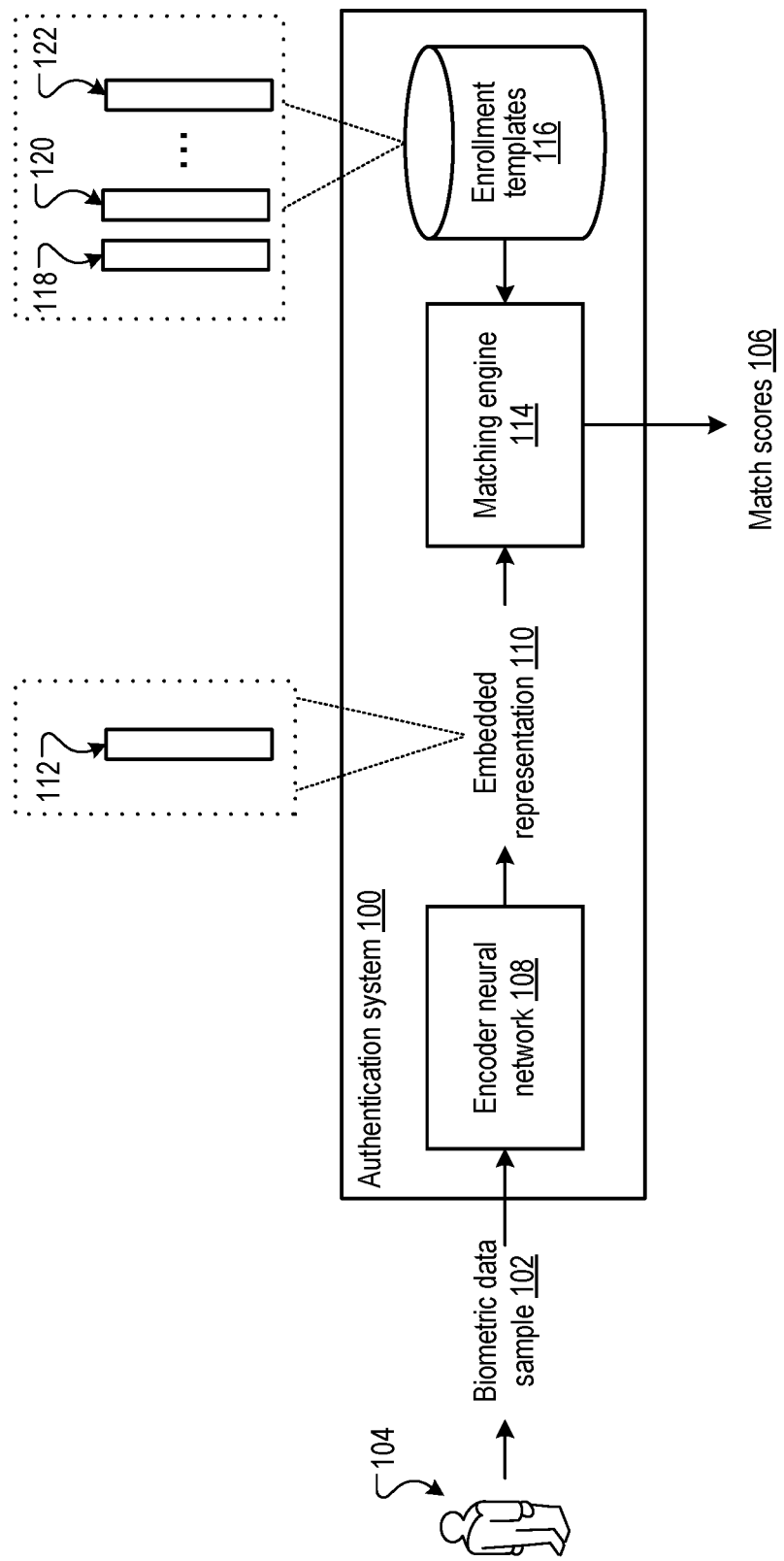
FIG. 1 is a block diagram of an example authentication system.

FIG. 1 shows an example authentication system 100. The authentication system 100 is an example of a system implemented as computer programs on one or more computers in one or more locations in which the systems, components, and techniques described below are implemented.

The authentication system 100 processes a biometric data sample 102 that characterizes the identity of a person 104 that submitted the biometric data sample to generate a set of one or more match scores 106. The biometric data sample 102 may be an image depicting the eye, the face, the palm print, or the fingerprint of the submitting person 104, an audio sample representing a spoken utterance of the submitting person 104, or any other biometric data characterizing the identity of the submitting person 104. The biometric data sample 102 may be obtained from the submitting person 104 using a camera, a microphone, or by any other appropriate sensor. The match scores 106 may include a respective numerical value for each of a predetermined set of one or more people (referred to herein as "authorized users"), where the numerical value corresponding to an authorized user indicates a likelihood that the person 104 has the same identity as the authorized user. The authorized users may be people who are authorized to access particular data or perform particular actions within, for example, a data storage system, a banking system, or an electronic medical records system, or people who are authorized to access particular physical locations (e.g., research facilities or warehouses).

The system 100 includes an encoder neural network 108 which is configured to process the biometric data sample 102 in accordance with current values of a set of encoder neural network parameters to generate as output an embedded representation 110 of the biometric data sample 102. The embedded representation 110 is a numerical representation of the biometric data sample 102 in any appropriate format (e.g., as a vector, as depicted by 112). As will be described in more detail later (e.g., with reference to FIG. 3), the embedded representation 110 may include an inter-class embedded representation and an intra-class embedded representation.

The encoder neural network 108 may be implemented as a convolutional neural network, a fully-connected neural network, a recurrent neural network, or in any other appropriate configuration that allows the neural network to process a biometric sample of the same type as the sample 102 to generate the embedded representation 110. In a particular example, the biometric data sample 102 may be an image (e.g., an image of the eye of the submitting person 104), the encoder neural network 108 may be a convolutional neural network, and the embedded representation may be a vector or matrix of feature outputs representing the biometric data sample 102.

The system 100 includes a matching engine 114 that is configured to process the embedded representation 110 and each of multiple enrollment templates 116 (e.g., the enrollment templates 118, 120, and 122) to determine the match scores 106. Each enrollment template 116 corresponds to a different authorized user and characterizes an expected embedded representation of a biometric data sample characterizing the identity of the authorized user. The matching engine 114 may determine the match scores 106 by computing a numerical measure of similarity between the embedded representation 110 and each of the enrollment templates 116. The numerical similarity measure between the embedded representation 110 and an enrollment template 116 may be a cosine similarity measure, a Euclidean distance, or any other appropriate numerical similarity or distance measure.

After generating the match scores 106, the system 100 may determine whether to identify the submitting person 104 as an authorized user based on the match scores 106 and, optionally, one or more additional data sources (e.g., a submitted password). For example, the system 100 may identify the person 104 as an authorized user if at least one of the match scores exceeds a predetermined threshold. In this example, if each of the match scores 106 is less than the predetermined threshold, the system 100 may refrain from identifying the person 104 as an authorized user.

Figure 2:
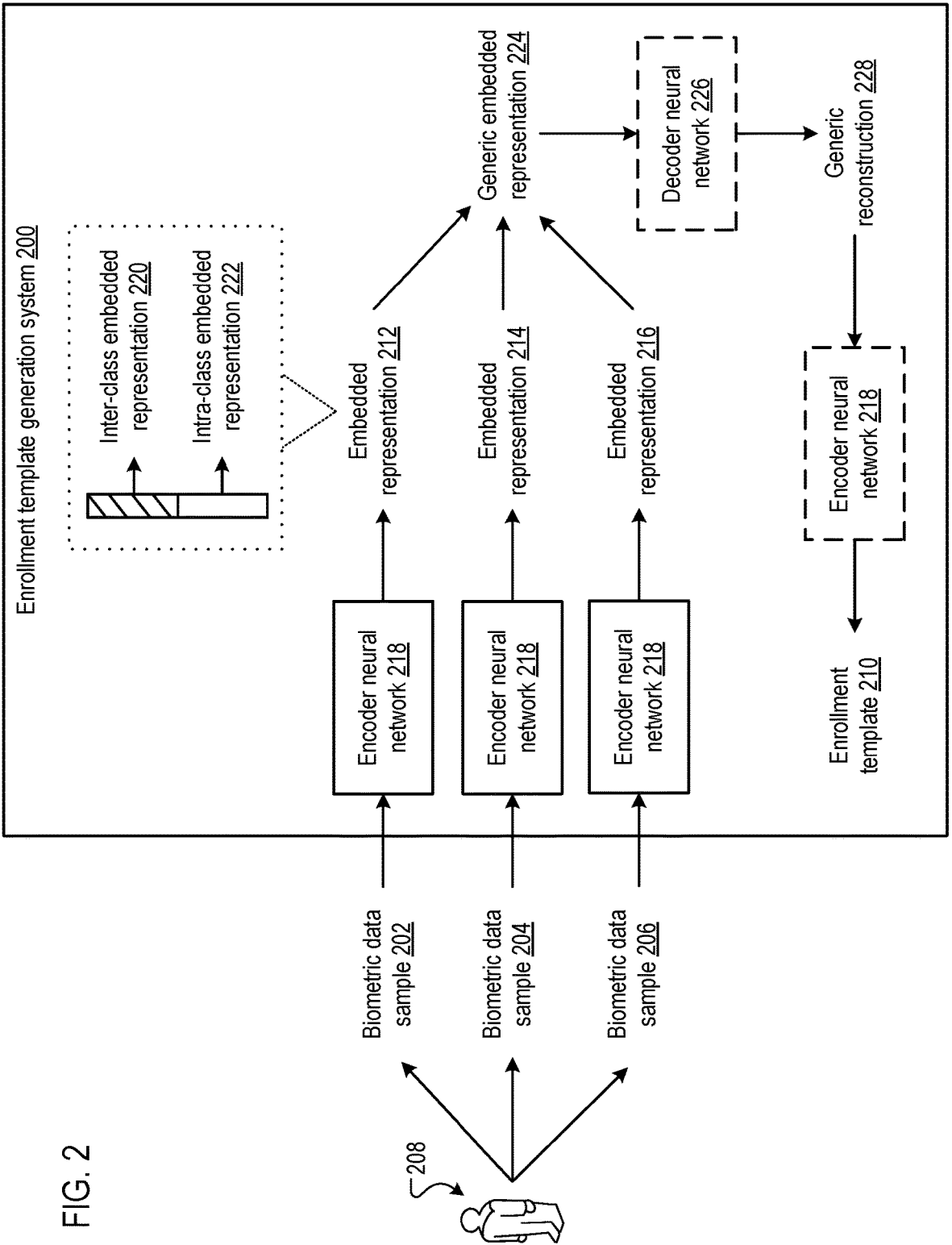
FIG. 2 is a block diagram of an example template generation system.

FIG. 2 shows an example enrollment template generation system 200. The enrollment template generation system 200 is an example of a system implemented as computer programs on one or more computers in one or more locations in which the systems, components, and techniques described below are implemented.

The enrollment template generation system 200 processes one or more biometric data samples (e.g., the biometric data samples 202, 204, and 206) that characterize the identity of a person 208 to generate an enrollment template 210 for the person 208. The enrollment template 210 characterizes an expected embedded representation of a biometric data sample that characterizes the identity of the person 208.

The one or more biometric data samples processed by the system 200 may be, for example, multiple images depicting an eye of the person 208. In this example, the images may differ due to, for example, differences in lighting, differences in camera angle, differences in the gaze angle of the eye, differences in image resolution, or differences in image quality (e.g., blurriness).

The system 200 generates a respective embedded representation (e.g., the embedded representations 212, 214, and 216) of each of the biometric data samples by processing each of the biometric data samples by an encoder neural network 218. Generally, processing a biometric data sample by the encoder neural network 218 refers to processing a numerical representation of the biometric data sample. For example, if the biometric data sample is an image, then the encoder neural network 218 may process a matrix of numerical values representing the colors and intensities of the pixels of the image.

Each embedded representation of a biometric data sample generated by the encoder neural network 218 includes: (i) a respective inter-class embedded representation and (ii) a respective intra-class embedded representation (which are, in general, different). For example, if an embedded representation is represented as a vector, then the inter-class embedded representation and the intra-class embedded representation may define a partition of the vector into two disjoint subsets (e.g., as depicted by 220 and 222).

The encoder neural network 218 can be trained to generate an inter-class embedded representation of a biometric data sample which can be understood to characterize features of the biometric data sample which are potentially invariant across different biometric data samples from the same person. For example, if a biometric data sample is an image of a face, then the inter-class embedded representation of the biometric data sample may implicitly characterize underlying structural features of the face (e.g., the distance between the eyes). The encoder neural network can be trained to generate an intra-class embedded representation of a biometric data sample which characterizes features of the biometric data sample which are potentially variable between different biometric data samples from the same person. For example, if a biometric data sample is an image of a face, then the intra-class embedded representation of the biometric data sample may implicitly characterize variable features of the face (e.g., hairstyle or the presence of glasses, facial hair, or a hat).

The system 200 determines a generic embedded representation 224 from the embedded representations of each of the biometric data samples. For example, the system 200 may determine the inter-class embedded representation included in the generic embedded representation 224 to be a combination (e.g., an average) of the respective inter-class embedded representations included in the embedded representations of each of the biometric data samples. In this example, the system 200 may determine the intra-class embedded representation included in the generic embedded representation 224 to be a predetermined intra-class embedded representation where each component of the intra-class representation has a same value (e.g., the value zero).

The system 200 includes a decoder neural network 226. As will be described further with reference to FIG. 3, the decoder neural network 226 is trained to process an embedded representation of a biometric data sample to generate as output an approximate reconstruction of the biometric data sample. The decoder neural network 226 can be implemented as a convolutional neural network, a fully-connected neural network, or in any other appropriate configuration that allows the decoder neural network 226 to process embedded representations of biometric data samples to generate approximate reconstructions of the biometric data samples. In a particular example, the decoder neural network 226 may be a de-convolutional neural network which is configured to process embedded representations of biometric images to generate approximate reconstructions of the biometric images. The system 200 provides the generic embedded representation 224 to the decoder neural network 226 which processes the generic embedded representation 224 in accordance with current values of decoder neural network parameters to generate a generic reconstruction 228.

The system 200 processes the generic reconstruction 228 using the encoder neural network 218 to generate an embedded representation of the generic reconstruction 228. Finally, the system 200 determines the enrollment template 210 for the person 208 to be the embedded representation of the generic reconstruction 228. In some implementations, the system 200 may directly determine the enrollment template 210 to be the generic embedded representation 224, rather than the embedded representation of the generic reconstruction 228.

When the encoder neural network 218 is used by an authentication system (e.g., the authentication system 100 described with reference to FIG. 1), the authentication system may use only the portion of the embedded representation and the enrollment template corresponding to the inter-class embedded representation in generating the match scores. More specifically, the authentication system may determine the match score between an embedded representation and an enrollment template by computing a numerical measure of similarity between the portion of the embedded representation and the portion of the enrollment template corresponding to the inter-class embedded representation.

Figure 3:
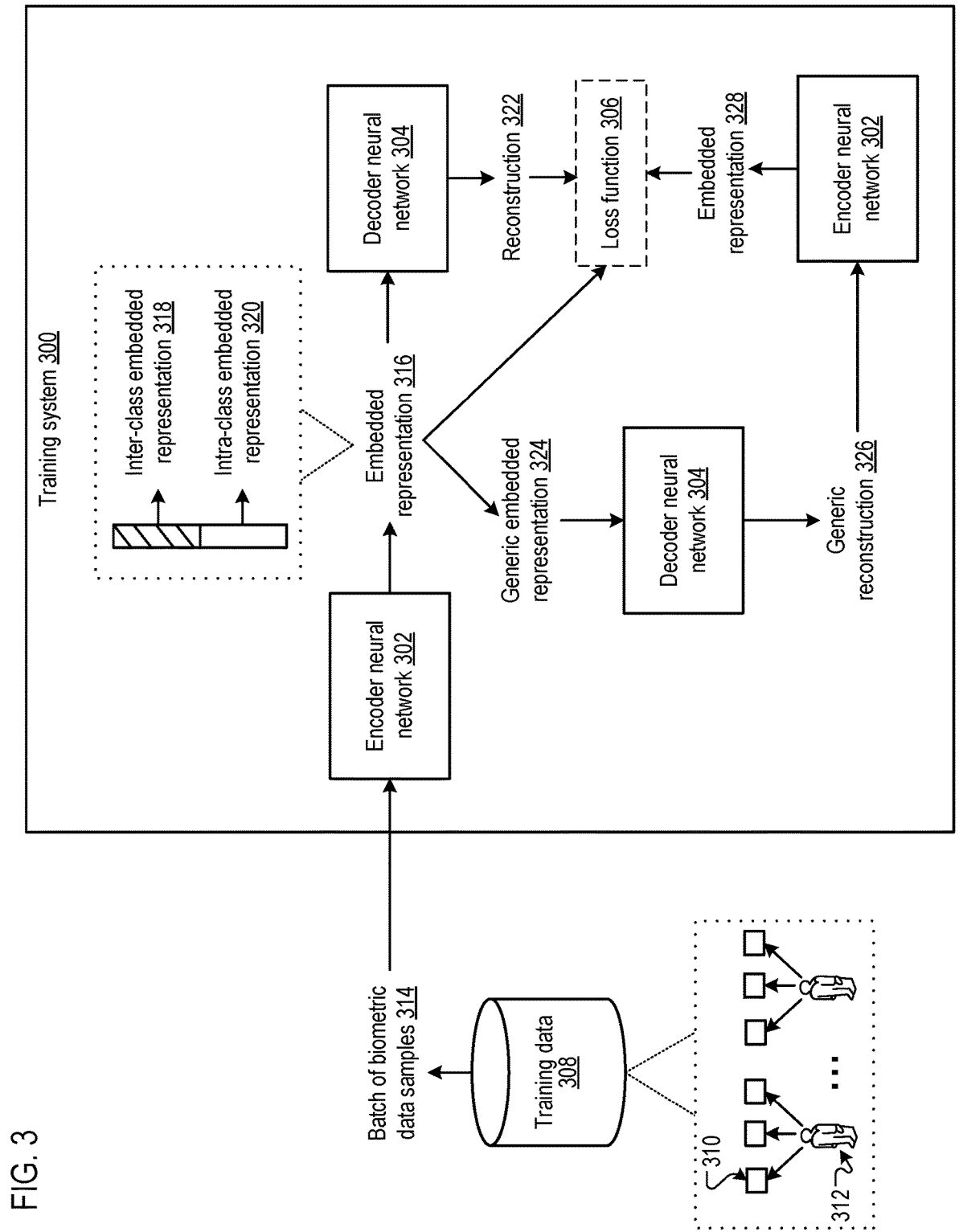
FIG. 3 is a block diagram of an example training system.

FIG. 3 is a block diagram of an example training system 300. The training system 300 is an example of a system implemented as computer programs on one or more computers in one or more locations in which the systems, components, and techniques described below are implemented.

The training system 300 is configured to train the encoder neural network 302 and the decoder neural network 304. The system 300 trains the encoder neural network 302 and the decoder neural network 304 by iteratively adjusting the values of the encoder neural network parameters and the decoder neural network parameters by gradients of a loss function 306 with respect to the encoder neural network parameters and the decoder neural network parameters.

After the encoder neural network 302 and the decoder neural network 304 are trained, the trained values of the encoder neural network parameters and the decoder neural network parameters can be provided for use in an authentication system 100 (e.g., as described with reference to FIG. 1) and an enrollment template generation system 200 (e.g., as described with reference to FIG. 2).

The encoder neural network 302 is configured to process a biometric data sample in accordance with current values of encoder neural network parameters to generate as output an embedded representation of the biometric data sample. Conversely, the decoder neural network 304 is configured to process an embedded representation of a biometric data sample to generate an approximate reconstruction of the biometric data sample.

The system 300 trains the encoder neural network 302 and the decoder neural network 304 based on a set of training data 308. The training data 308 includes multiple different biometric data samples (e.g., the biometric data sample 310) characterizing the identities of each of multiple different people (e.g., the person 312). The different biometric data samples included in the training data 308 characterizing the identity of a given person may be different images of a particular eye of the person (e.g., the person's left eye or right eye). The images may differ due to, for example, differences in lighting, differences in camera angle, differences in the direction of the gaze of the eye, differences in image resolution, differences in facial expression, makeup, differences in age or differences in image quality (e.g., blurriness).

The system 300 trains the encoder neural network 302 and the decoder neural network 304 over multiple training iterations. At each training iteration, the system 300 samples a batch (i.e., a set) of biometric data samples 314 from the training data 308. The batch of biometric data samples 314 includes one or biometric data samples that characterize the identity of a first person, referred to herein as "positive" (or "anchor") biometric data samples. The batch of biometric data samples 314 further includes one or more biometric data samples that characterize the identities of other people that are different than the first person, referred to herein as "negative" biometric data samples.

The system 300 processes each biometric data sample in the batch of biometric data samples 314 using the encoder neural network 302 in accordance with current values of encoder neural network parameters to generate a respective embedded representation 316 of each biometric data sample in the batch 314. As described earlier, each embedded representation 316 includes an inter-class embedded representation and an intra-class embedded representation (e.g., as depicted by 318 and 320).

As will be described further with reference to FIG. 4, the loss function 306 includes one or more terms that each correspond to a respective pair of biometric data samples in the batch 314, where the pair includes a positive biometric data sample and a negative biometric data sample. Each of these loss function terms encourage the inter-class embedded representations of the corresponding positive and negative biometric data samples to be less similar than the embedded representations of the corresponding positive and negative biometric data samples. Generally, the system 300 may determine the similarity between pairs of embedded representations (or pairs of inter-class embedded representations) by a cosine similarity measure, a Euclidean distance, or by any other appropriate numerical similarity or distance measure.

As will be described further with reference to FIG. 4, the loss function may further include one or more terms that each correspond to a respective pair of positive biometric data samples in the batch 314. Each of these loss function terms encourages the inter-class embedded representations of the corresponding positive biometric data samples to be more similar than the embedded representations of the corresponding positive biometric data samples.

The system 300 may process the embedded representation 316 of each biometric data sample in the batch 314 using the decoder neural network 304 in accordance with current values of decoder neural network parameters to generate a respective approximate reconstruction 322 of each biometric data sample in the batch 314. As will be described further below with reference to FIG. 5, the loss function 306 may include one or more terms that each correspond to a respective reconstruction 322 of a biometric data sample in the batch 314. Each of these loss function terms encourage the reconstruction 322 to be more similar to the corresponding biometric data sample (i.e., to increase the fidelity of the reconstruction of the biometric data sample).

The system 300 may determine a generic embedded representation 324 from the inter-class embedded representations of the positive biometric data samples in the batch 314. For example, the system 300 may determine the inter-class embedded representation included in the generic embedded representation 324 to be a combination (e.g., an average) of the respective inter-class embedded representations included in the embedded representations of each of the positive biometric data samples. In this example, the system 300 may determine the intra-class embedded representation included in the generic embedded representation 324 to be a predetermined intra-class embedded representation where each component of the intra-class representation has a same value (e.g., the value zero).

The system 300 may process the generic embedded representation 324 by the decoder neural network in accordance with current values of decoder neural network parameters to generate a generic reconstruction 326 of the generic embedded representation 324. The system 300 may process the generic reconstruction 326 by the encoder neural network 302 in accordance with current values of encoder neural network parameters to generate an embedded representation 328 of the generic reconstruction 326.

As will be described further with reference to FIG. 6, the loss function 306 may further include one or more terms that encourage the inter-class embedded representation of the generic reconstruction 326 and the inter-class embedded representations of the negative biometric data samples in the batch 314 to be less similar. The loss function 306 may further include one or more terms that encourage the inter-class embedded representation of the generic reconstruction 326 and the inter-class embedded representation of the positive biometric data samples included in the batch 314 to be more similar.

The system 300 may train the encoder neural network 302 and the decoder neural network 304 until a termination criterion is met. For example, the termination criterion may be that the system 300 has trained the encoder neural network 302 and the decoder neural network 304 for a predetermined maximum number of iterations. As another example, the termination criterion may be that the change in the value of the loss function 306 between training iterations is below a predetermined threshold.

Figure 4:
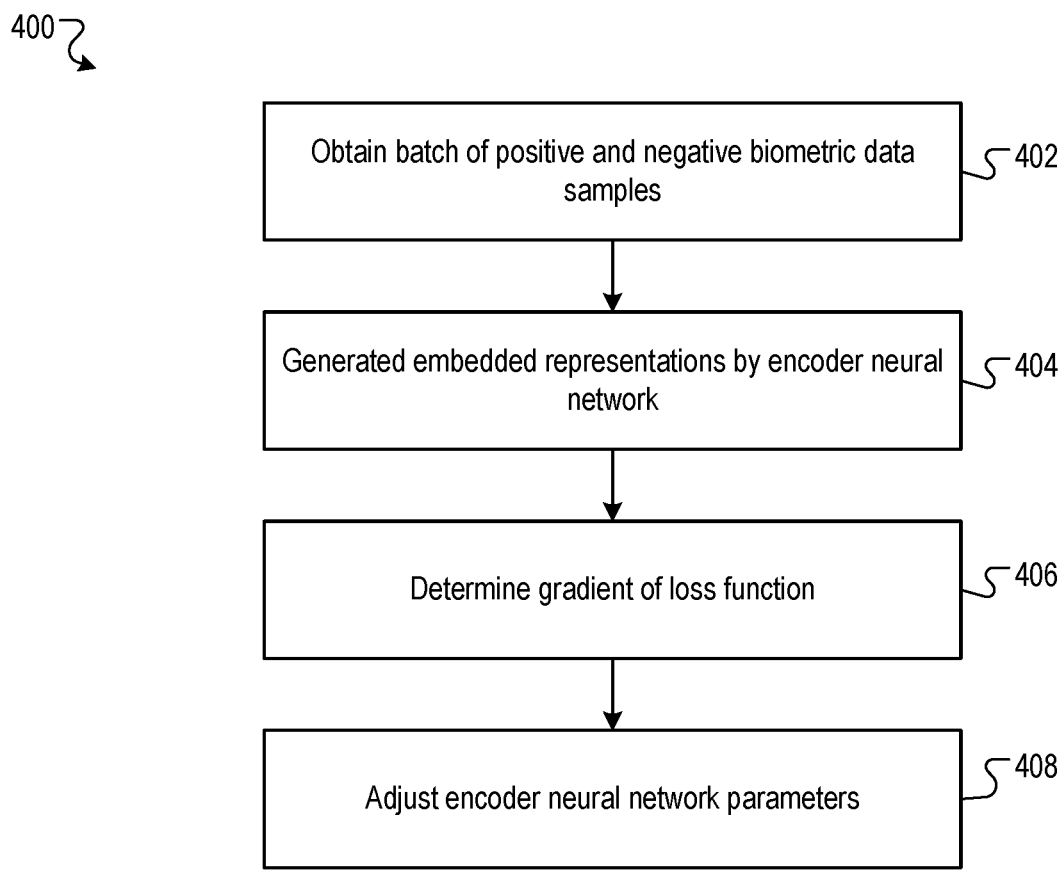
FIG. 4 is a flow diagram of an example process for adjusting encoder neural network parameters based on embedded representations of biometric data samples.

FIG. 4 is a flow diagram of an example process 400 for adjusting encoder neural network parameters based on embedded representations of biometric data samples. More specifically, FIG. 4 describes one iteration of an example iterative process (which generally includes multiple iterations) for training an encoder neural network. For convenience, the process 400 will be described as being performed by a system of one or more computers located in one or more locations. For example, a training system, e.g., the training system 300 of FIG. 3, appropriately programmed in accordance with this specification, can perform the process 400.

The system obtains a batch of biometric data samples from a set of training data, including one or more positive biometric data samples and one or more negative biometric data samples (402). Each positive biometric data sample characterizes the identity of the same first person, and each negative biometric data sample characterizes the identity of a respective person different than the first person.

The system may obtain the batch by sampling from a set of training data that includes multiple different biometric data samples characterizing the identities of each of multiple different people. In some cases, if the training data includes fewer than a threshold number of biometric data samples characterizing the identity of a given person, the system may augment the training data by including more biometric data samples characterizing the identity of the given person. For example, the system may augment the training data by including one or more synthetic biometric data samples characterizing the identity of the given person. The system can generate a synthetic biometric data sample by distorting (e.g., by adding noise or randomly rotating) a biometric data sample characterizing the identity of the given person.

The system processes each biometric data sample in the batch of biometric data samples using the encoder neural network in accordance with current values of encoder neural network parameters to generate a respective embedded representation of each biometric data sample (404). Generally, processing a biometric data sample by the encoder neural network refers to processing a numerical representation of the biometric data sample. For example, if the biometric data sample is an image, then the encoder neural network may process a matrix of numerical values representing the colors and intensities of the pixels of the image. As another example, if the biometric data sample is an audio sample, then the encoder neural network may process a vector of numerical values representing the time-varying amplitude of the audio signal included in the audio sample. The encoder neural network may be implemented as a convolutional neural network, a fully-connected neural networks, or in any other configuration.

Each embedded representation of a biometric data sample generated by the encoder neural network includes: (i) a respective inter-class embedded representation and (ii) a respective intra-class embedded representation (which are, in general, different). For example, if an embedded representation is represented as a vector, then the inter-class embedded representation and the intra-class embedded representation may define a partition of the vector into two disjoint sub sets.

The system determines a gradient of a loss function with respect to the encoder neural network parameters (406). The system may determine the gradient of the loss function by backpropagation, or by any other appropriate method. The loss function includes one or more terms that each correspond to a respective pair of biometric data samples in the batch, where the pair includes a positive biometric data sample and a negative biometric data sample. Each of these loss function terms encourage the inter-class embedded representations of the corresponding positive and negative biometric data samples to be less similar than the embedded representations of the corresponding positive and negative biometric data samples. For example, the loss function $\mathcal{L}$ may include the terms:

$$\sum_{i,j=1}^{N} (\max(0, \mathbb{I}_{i,j} - T) + \max(0, \mathbb{I}_{i,j}^{inter} - T + \epsilon)) \qquad (1)$$

where N is the number of positive and negative biometric data samples in the batch, T and $\epsilon$ are positive numbers (e.g., both between 0 and 1), and for each i and each j, $\mathbb{I}_{i,j} = S(P_i, N_j)$, where $P_i$ is the embedded representation of the i-th positive biometric data sample, $N_j$ is the embedded representation of the j-th negative biometric data sample, $S(\cdot,\cdot)$ is a similarity measure (e.g., a cosine similarity measure), $\mathbb{I}_{i,j}^{inter} = S(P_i^{inter}, N_j^{inter})$, where $P_i^{inter}$ is the inter-class embedded representation of the i-th positive biometric data sample, and $N_j^{inter}$ is the inter-class embedded representation of the j-th negative biometric data sample.

The loss function may further include one or more terms that each correspond to a respective pair of positive biometric data samples in the batch. Each of these loss function terms encourages the inter-class embedded representations of the corresponding positive biometric data samples to be more similar than the embedded representations of the corresponding positive biometric data samples. For example, the loss function $\mathcal{L}$ may include the terms:

$$\sum_{i,j=1}^{N} (\max(0, T - \mathbb{C}_{i,j}) + \max(0, T + \epsilon - \mathbb{C}_{ij}^{inter})) \qquad (2)$$

where N is the number of positive and negative biometric data samples in the batch, T and E are positive numbers (e.g., both between 0 and 1), and for each i and each j, $\mathbb{G}_{i,j}=S(P_i, P_j)$, where $P_i$ is the embedded representation of the i-th positive biometric data sample, $P_j$ is the embedded representation of the j-th positive biometric data sample, $S(\cdot,\cdot)$ is a similarity measure (e.g., a cosine similarity measure), $\mathbb{G}_{i,j}^{inter}=S(P_i^{inter}, P_j^{inter})$, where $P_i^{inter}$ is the inter-class embedded representation of the i-th positive biometric data sample, and $P_j^{inter}$ is the inter-class embedded representation of the j-th positive biometric data sample.

The system adjusts the current values of the encoder neural network parameters using the gradient (408). The system can use the gradient to adjust the current values of the encoder neural network parameters using any appropriate gradient descent optimization algorithm update rule. Examples of gradient descent optimization algorithms include Adam, RMSprop, Adagrad, Adadelta, and AdaMax, amongst others.

Figure 5:
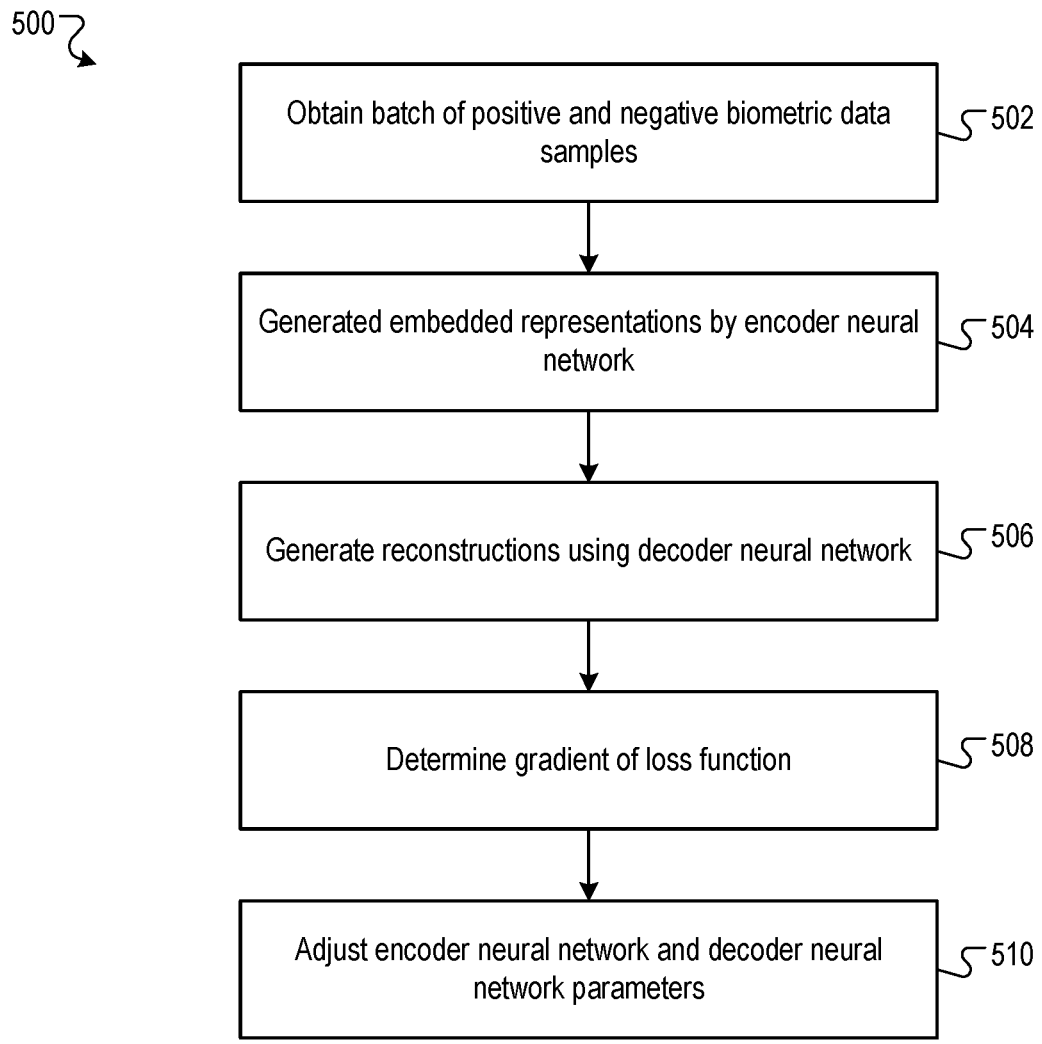
FIG. 5 is a flow diagram of an example process for adjusting encoder neural network and decoder neural network parameters based on reconstructions of biometric data samples.

FIG. 5 is a flow diagram of an example process 500 for adjusting encoder neural network and decoder neural network parameters based on reconstructions of biometric data samples. More specifically, FIG. 5 describes one iteration of an example iterative process for training an encoder neural network and a decoder neural network. For convenience, the process 500 will be described as being performed by a system of one or more computers located in one or more locations. For example, a training system, e.g., the training system 300 of FIG. 3, appropriately programmed in accordance with this specification, can perform the process 500.

The system obtains a batch of biometric data samples from a set of training data (e.g., including positive and negative biometric data samples, as described earlier) (502). Obtaining a batch of biometric data samples is described further with reference to 402.

The system processes each biometric data sample in the batch of biometric data samples using the encoder neural network, in accordance with current values of encoder neural network parameters, to generate a respective embedded representation of each biometric data sample (504). Generating embedded representations of biometric data samples is described further with reference to 404.

The system processes the embedded representation of each biometric data sample using the decoder neural network, in accordance with current values of decoder neural network parameters, to generate a respective approximate reconstruction of each biometric data sample in the batch (506). The decoder neural network may be implemented as a convolutional neural network, a fully-connected neural network, or in any other configuration.

The system determines a gradient of a loss function with respect to the encoder neural network parameters and decoder neural network parameters (508). The system may determine the gradient of the loss function by backpropagation, or by any other appropriate method. The loss function may include one or more terms that each correspond to respective reconstruction of a biometric data sample in the batch. Each of these loss function terms encourage the reconstruction to be more similar to the corresponding biometric data sample (i.e., to increase the fidelity of the reconstruction of the biometric data sample). For example, the loss function $\mathcal{L}$ may include the terms:

$$\sum_{i=1}^{2 \cdot N} |I_i - \overline{I}_i|_2^2 \quad (4)$$

where $2 \cdot N$ is the total number of biometric data samples in the batch (e.g., with N positive biometric data samples and N negative biometric data samples), $I_i$ is the i-th biometric data sample in the batch, $\overline{I}_i$ is the reconstruction of the i-th biometric data sample in the batch (i.e., as described with reference to 506), and $|\cdot|_2^2$ refers to the squared $L^2$ distance. For example, if A is a matrix, then $|A|_2^2$ is the sum of the squares of each component of the matrix A.

The system adjusts the current values of the encoder neural network parameters and the decoder neural network parameters using the gradient (510). Adjusting the parameters of a neural network using a gradient is described further with reference to 408.

Figure 6:
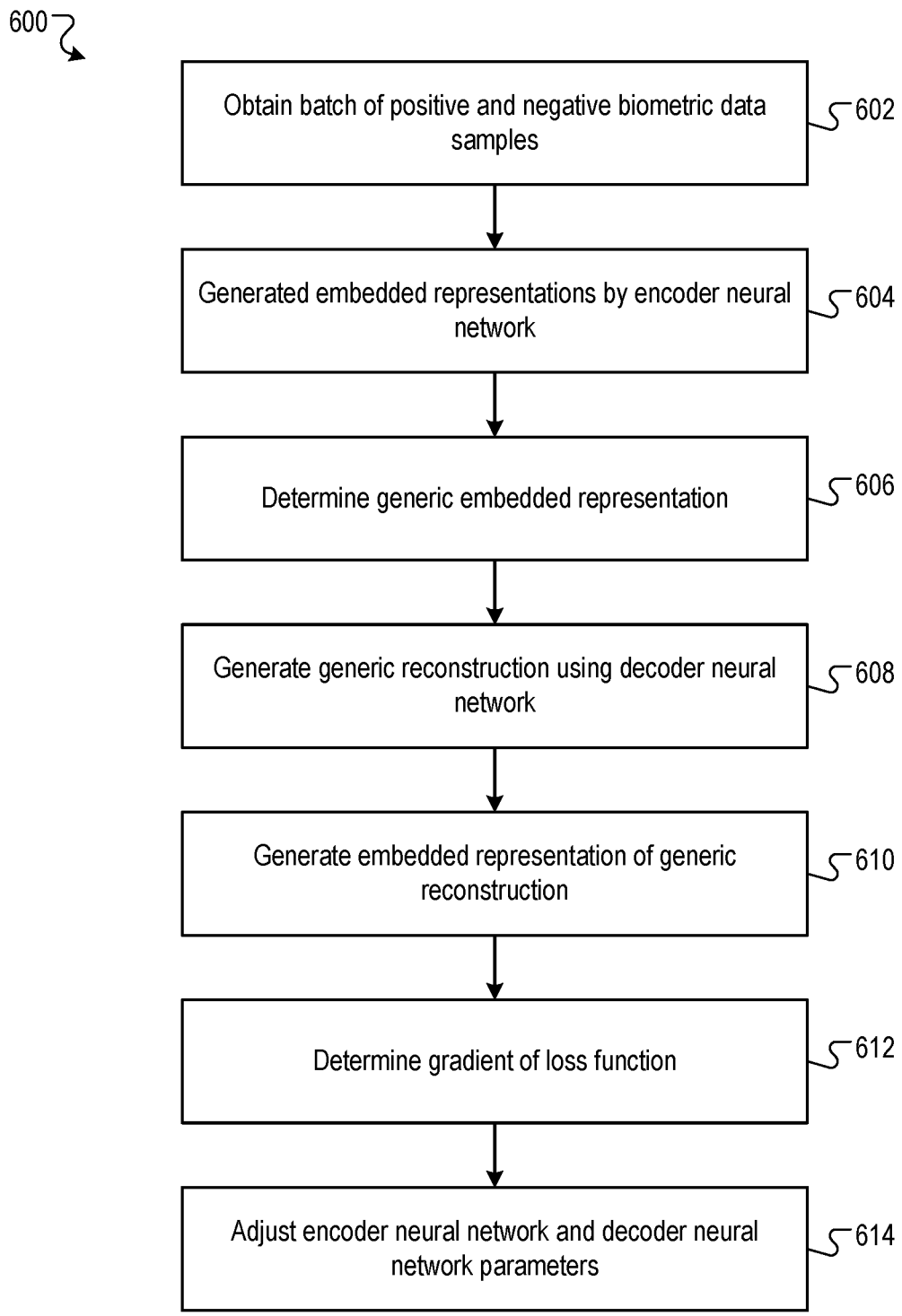
FIG. 6 is a flow diagram of an example process for adjusting encoder neural network and decoder neural network parameters based on embedded representations of reconstructions of biometric data samples.

FIG. 6 is a flow diagram of an example process 600 for adjusting encoder neural network and decoder neural network parameters based on embedded representations of reconstructions of biometric data samples. More specifically, FIG. 6 describes one iteration of an example iterative process for training an encoder neural network and a decoder neural network. For convenience, the process 600 will be described as being performed by a system of one or more computers located in one or more locations. For example, a training system, e.g., the training system 300 of FIG. 3, appropriately programmed in accordance with this specification, can perform the process 600.

The system obtains a batch of biometric data samples from a set of training data, including one or more positive biometric data samples and one or more negative biometric data samples (602). Obtaining a batch of biometric data samples is described further with reference to 402.

The system processes each biometric data sample in the batch of biometric data samples using the encoder neural network in accordance with current values of encoder neural network parameters to generate a respective embedded representation of each biometric data sample (604). Generating embedded representations of biometric data samples is described further with reference to 404.

The system determines a generic embedded representation from the inter-class embedded representations of the positive biometric data samples in the batch (606). In some cases, the system may determine the inter-class embedded representation included in the generic embedded representation to be a combination (e.g., an average) of the respective inter-class embedded representations included in the embedded representations of each of the positive biometric data samples. In some cases, the system may determine the intra-class embedded representation included in the generic embedded representation to be a predetermined intra-class embedded representation where each component of the intra-class representation has a same value (e.g., the value zero).

The system processes the generic embedded representation by the decoder neural network in accordance with current values of decoder neural network parameters to generate a generic reconstruction of the generic embedded representation (608). Next, the system processes the generic reconstruction by the encoder neural network in accordance with current values of encoder neural network parameters to generate an embedded representation of the generic reconstruction (610). The embedded representation of the generic reconstruction includes an inter-class embedded representation of the generic reconstruction and an intra-class embedded representation of the generic reconstruction.

The system determines a gradient of a loss function with respect to the encoder neural network parameters and the decoder neural network parameters (612). The system may determine the gradient of the loss function by backpropagation, or by any other appropriate method. The loss function may include one or more terms that encourage the inter-class embedded representation of the generic reconstruction and the inter-class embedded representations of the negative biometric data samples in the batch to be less similar. For example, the loss function $\mathcal{L}$ may include the terms:

$$\sum_{i=1}^{N} \max(0, \overline{\mathbb{I}}_i^{inter} - T \mp \epsilon) \quad (5)$$

where N is the number of negative biometric data samples in the batch, $\overline{\mathbb{I}}_i^{inter} = S(R^{inter}, N_i^{inter})$, where $R^{inter}$ is the inter-class embedded representation of the generic reconstruction, $N_i^{inter}$ is the inter-class embedded representation of the i-th negative biometric data sample, $S(\cdot,\cdot)$ is a similarity measure (e.g., a cosine similarity measure), and T and $\epsilon$ are positive numbers (e.g., both between 0 and 1).

The loss function may further include one or more terms that encourage the inter-class embedded representation of the generic reconstruction and the inter-class embedded representation of the positive biometric data samples included in the batch to be more similar. For example, the loss function $\mathcal{L}$ may include the terms:

$$\sum_{i=1}^{N} \max(0, T + \epsilon - \overline{\mathbb{G}}_i^{inter}) \quad (6)$$

where N is the number of negative biometric data samples in the batch, $\overline{\mathbb{G}}_i^{inter} = S(R^{inter}, P_i^{inter})$, where $R^{inter}$ is the inter-class embedded representation of the generic reconstruction, $P_i^{inter}$ is the inter-class embedded representation of the i-th positive biometric data sample, $S(\cdot,\cdot)$ is a similarity measure (e.g., a cosine similarity measure), and T and $\epsilon$ are positive numbers (e.g., both between 0 and 1).

The system adjusts the current values of the encoder neural network parameters and the decoder neural network parameters using the gradient (614). Adjusting the parameters of a neural network using a gradient is described further with reference to 408.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a PyTorch, a Torch, a Caffe, a Caffe2, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for training an encoder neural network having a plurality of encoder neural network parameters and being configured to process a biometric data sample in accordance with current values of encoder neural network parameters to generate as output an embedded representation of the biometric data sample, wherein the embedded representation of the biometric data sample defines a set of features representing the biometric data sample, the method comprising:
  obtaining a positive biometric data sample characterizing an identity of a first person and a negative biometric data sample characterizing an identity of a second person, wherein the identity of the first person is different than the identity of the second person;

processing the positive biometric data sample and the negative biometric data sample using the encoder neural network and in accordance with the current values of the encoder neural network parameters to generate: (i) an embedded representation of the positive biometric data sample that defines a set of features representing the positive biometric data sample, and (ii) an embedded representation of the negative biometric sample that defines a set of features representing the negative biometric data sample;

determining a gradient of a loss function with respect to the encoder neural network parameters, wherein the loss function includes a first term that encourages a similarity between: (i) a specified proper subset of the set of features defined by the embedded representation of the positive biometric data sample and (ii) a corresponding specified proper subset of the set of features defined by the embedded representation of the negative biometric data sample, to be less than a similarity between: (i) the set of features defined by the embedded representation of the positive biometric data sample and (ii) the set of features defined by the embedded representation of the negative biometric data sample; and adjusting the current values of the encoder neural network parameters using the gradient of the loss function.

2. The method of claim 1, further comprising:

obtaining an additional positive biometric data sample characterizing the identity of the first person;

processing the additional positive biometric data sample using the encoder neural network and in accordance with the current values of the encoder neural network parameters to generate an embedded representation of the additional positive biometric data sample that defines a set of feature representing the additional positive biometric data sample;

wherein the loss function includes a second term that encourages a similarity between: (i) a corresponding specified proper subset of the set of features defined by the embedded representation of the additional positive biometric data sample and (ii) the specified proper subset of the set of features defined by the embedded representation of the positive biometric data sample, to be greater than a similarity between: (i) the set of features defined by the embedded representation of the additional positive biometric data sample and (ii) the set of features defined by the embedded representation of the positive biometric data sample.

3. The method of claim 1, further comprising jointly training the encoder neural network and a decoder neural network, wherein the decoder neural network has a plurality of decoder neural network parameters and is configured to process an embedded representation of a biometric data sample in accordance with current values of decoder neural network parameters to generate as output a reconstruction of the biometric data sample, the joint training comprising:

processing the embedded representation of the positive biometric data sample and the embedded representation of the negative biometric data sample using the decoder neural network and in accordance with the current values of the decoder neural network parameters to generate a reconstruction of the positive biometric data sample and a reconstruction of the negative biometric data sample;

determining a gradient of the loss function with respect to the decoder neural network parameters, wherein the loss function includes one or more third terms that encourage the positive biometric data sample and the reconstruction of the positive biometric data sample to be more similar and that encourage the negative biometric data sample and the reconstruction of the negative biometric data sample to be more similar; and adjusting the current values of the decoder neural network parameters using the gradient of the loss function.

4. The method of claim 3, further comprising:

determining a generic embedded representation from the embedded representation of the positive biometric data sample that defines a set of features representing the positive biometric data sample;

processing the generic embedded representation using the decoder neural network and in accordance with the current values of the decoder neural network parameters to generate a generic reconstruction;

processing the generic reconstruction using the encoder neural network and in accordance with the current values of the encoder neural network parameters to generate an embedded representation of the generic reconstruction that defines a set of features representing the generic reconstruction;

wherein the loss function includes one or more fourth terms that encourage a corresponding specified proper subset of the set of features defined by the embedded representation of the generic reconstruction and the specified proper subset of the set of features defined by the embedded representation of the negative biometric data sample to be less similar and that encourage the specified proper subset of the set of features defined by the embedded representation of the generic reconstruction and the specified proper subset of the set of features defined by the embedded representation of the positive biometric data sample to be more similar.

5. The method of claim 4, wherein determining a generic embedded representation from the embedded representation of the positive biometric data sample comprises:

determining a first proper subset of the set of features defined by the generic embedded representation by averaging the specified proper subset of the set of features defined by the embedded representation of the positive biometric data sample and corresponding specified proper subsets of sets of features defined by embedded representations of one or more additional positive biometric data samples.

6. The method of claim 5, wherein determining a generic embedded representation from the embedded representation of the positive biometric data sample comprises:

determining that each component of a second proper subset of the set of features defined by the generic embedded representation has a same predetermined value, wherein the first proper subset of the set of features defined by the generic embedded representation and the second proper subset of the set of features defined by the generic embedded representation form a partition of the generic embedded representation.

7. The method of claim 1, wherein each biometric data sample is an image depicting an eye of a person who is a source of the biometric data sample.

8. The method of claim 7, wherein the encoder neural network is a convolutional neural network.

9. The method of claim 1, wherein similarity is measured based on a cosine similarity measure.

10. A system, comprising:

a data processing apparatus;

a memory in data communication with the data processing apparatus and storing instructions that cause the data processing apparatus to train an encoder neural network having a plurality of encoder neural network parameters and being configured to process a biometric data sample in accordance with current values of encoder neural network parameters to generate as output an embedded representation of the biometric data sample, wherein the embedded representation of the biometric data sample defines a set of features representing the biometric data sample, the training comprising:

obtaining a positive biometric data sample characterizing an identity of a first person and a negative biometric data sample characterizing an identity of a second person, wherein the identity of the first person is different than the identity of the second person;

processing the positive biometric data sample and the negative biometric data sample using the encoder neural network and in accordance with the current values of the encoder neural network parameters to generate: (i) an embedded representation of the positive biometric data sample that defines a set of features representing the positive biometric data sample, and (ii) an embedded representation of the negative biometric sample that defines a set of features representing the negative biometric data sample;

determining a gradient of a loss function with respect to the encoder neural network parameters, wherein the loss function includes a first term that encourages a similarity between: (i) a specified proper subset of the set of features defined by the embedded representation of the positive biometric data sample and (ii) a corresponding specified proper subset of the set of features defined by the embedded representation of the negative biometric data sample, to be less than a similarity between: (i) the set of features defined by the embedded representation of the positive biometric data sample and (ii) the set of features defined by the embedded representation of the negative biometric data sample; and adjusting the current values of the encoder neural network parameters using the gradient of the loss function.

11. The system of claim 10, wherein the training further comprises:

obtaining an additional positive biometric data sample characterizing the identity of the first person;

processing the additional positive biometric data sample using the encoder neural network and in accordance with the current values of the encoder neural network parameters to generate an embedded representation of the additional positive biometric data sample that defines a set of feature representing the additional positive biometric data sample;

wherein the loss function includes a second term that encourages a similarity between: (i) a corresponding specified proper subset of the set of features defined by the embedded representation of the additional positive biometric data sample and (ii) the specified proper subset of the set of features defined by the embedded representation of the positive biometric data sample, to be greater than a similarity between: (i) the set of features defined by the embedded representation of the additional positive biometric data sample and (ii) the set of features defined by the embedded representation of the positive biometric data sample.

12. The system of claim 10, wherein the instructions further cause the data processing apparatus to jointly train the encoder neural network and a decoder neural network, wherein the decoder neural network has a plurality of decoder neural network parameters and is configured to process an embedded representation of a biometric data sample in accordance with current values of decoder neural network parameters to generate as output a reconstruction of the biometric data sample, the joint training comprising:

processing the embedded representation of the positive biometric data sample and the embedded representation of the negative biometric data sample using the decoder neural network and in accordance with the current values of the decoder neural network parameters to generate a reconstruction of the positive biometric data sample and a reconstruction of the negative biometric data sample;

determining a gradient of the loss function with respect to the decoder neural network parameters, wherein the loss function includes one or more third terms that encourage the positive biometric data sample and the reconstruction of the positive biometric data sample to be more similar and that encourage the negative biometric data sample and the reconstruction of the negative biometric data sample to be more similar; and adjusting the current values of the decoder neural network parameters using the gradient of the loss function.

13. The system of claim 12, wherein the joint training further comprises:

determining a generic embedded representation from the embedded representation of the positive biometric data sample that defines a set of features representing the positive biometric data sample;

processing the generic embedded representation using the decoder neural network and in accordance with the current values of the decoder neural network parameters to generate a generic reconstruction;

processing the generic reconstruction using the encoder neural network and in accordance with the current values of the encoder neural network parameters to generate an embedded representation of the generic reconstruction that comprises a set of features representing the generic reconstruction;

wherein the loss function includes one or more fourth terms that encourage a corresponding specified proper subset of the set of features defined by the embedded representation of the generic reconstruction and the specified proper subset of the set of features defined by the embedded representation of the negative biometric data sample to be less similar and that encourage the specified proper subset of the set of features defined by the embedded representation of the generic reconstruction and the specified proper subset of the set of features defined by the embedded representation of the positive biometric data sample to be more similar.

14. The system of claim 13, wherein determining a generic embedded representation from the embedded representation of the positive biometric data sample comprises:

determining a first proper subset of the set of features defined by the generic embedded representation by averaging the specified proper subset of the set of features defined by the embedded representation of the positive biometric data sample and corresponding specified proper subsets of sets of features defined by embedded representations of one or more additional positive biometric data samples.

15. The system of claim 14, wherein determining a generic embedded representation from the embedded representation of the positive biometric data sample comprises:

determining that each component of a second proper subset of the set of features defined by the generic embedded representation has a same predetermined value, wherein the first proper subset of the set of features defined by the generic embedded representation and the second proper subset of the set of features defined by the generic embedded representation form a partition of the generic embedded representation.

16. One or more non-transitory computer storage media storing instructions that when executed by one or more computers cause the one or more computers to train an encoder neural network having a plurality of encoder neural network parameters and being configured to process a biometric data sample in accordance with current values of encoder neural network parameters to generate as output an embedded representation of the biometric data sample, wherein the embedded representation of the biometric data sample defines a set of features representing the biometric data sample, the training comprising:
 obtaining a positive biometric data sample characterizing an identity of a first person and a negative biometric data sample characterizing an identity of a second person, wherein the identity of the first person is different than the identity of the second person;
 processing the positive biometric data sample and the negative biometric data sample using the encoder neural network and in accordance with the current values of the encoder neural network parameters to generate: (i) an embedded representation of the positive biometric data sample that defines a set of features representing the positive biometric data sample, and (ii) an embedded representation of the negative biometric sample that defines a set of features representing the negative biometric data sample;
 determining a gradient of a loss function with respect to the encoder neural network parameters, wherein the loss function includes a first term that encourages a similarity between: (i) a specified proper subset of the set of features defined by the embedded representation of the positive biometric data sample and (ii) a corresponding specified proper subset of the set of features defined by the embedded representation of the negative biometric data sample, to be less than a similarity between: (i) the set of features defined by the embedded representation of the positive biometric data sample and (ii) the set of features defined by the embedded representation of the negative biometric data sample; and
 adjusting the current values of the encoder neural network parameters using the gradient of the loss function.

17. The non-transitory computer storage media of claim 16, wherein the training further comprises:
 obtaining an additional positive biometric data sample characterizing the identity of the first person;
 processing the additional positive biometric data sample using the encoder neural network and in accordance with the current values of the encoder neural network parameters to generate an embedded representation of the additional positive biometric data sample that defines a set of feature representing the additional positive biometric data sample;
 wherein the loss function includes a second term that encourages a similarity between: (i) a corresponding specified proper subset of the set of features defined by the embedded representation of the additional positive biometric data sample and (ii) the specified proper subset of the set of features defined by the embedded representation of the positive biometric data sample, to be greater than a similarity between: (i) the set of features defined by the embedded representation of the additional positive biometric data sample and (ii) the set of features defined by the embedded representation of the positive biometric data sample.

18. The non-transitory computer storage media of claim 16, wherein when executed by the one or more computers, the instructions further cause the one or more computers to jointly train the encoder neural network and a decoder neural network, wherein the decoder neural network has a plurality of decoder neural network parameters and is configured to process an embedded representation of a biometric data sample in accordance with current values of decoder neural network parameters to generate as output a reconstruction of the biometric data sample, the joint training comprising:
 processing the embedded representation of the positive biometric data sample and the embedded representation of the negative biometric data sample using the decoder neural network and in accordance with the current values of the decoder neural network parameters to generate a reconstruction of the positive biometric data sample and a reconstruction of the negative biometric data sample;
 determining a gradient of the loss function with respect to the decoder neural network parameters, wherein the loss function includes one or more third terms that encourage the positive biometric data sample and the reconstruction of the positive biometric data sample to be more similar and that encourage the negative biometric data sample and the reconstruction of the negative biometric data sample to be more similar; and
 adjusting the current values of the decoder neural network parameters using the gradient of the loss function.

19. The non-transitory computer storage media of claim 18, wherein the joint training further comprises:
 determining a generic embedded representation from the embedded representation of the positive biometric data sample that defines a set of features representing the positive biometric data sample;
 processing the generic embedded representation using the decoder neural network and in accordance with the current values of the decoder neural network parameters to generate a generic reconstruction;
 processing the generic reconstruction using the encoder neural network and in accordance with the current values of the encoder neural network parameters to generate an embedded representation of the generic reconstruction that defines a set of features representing the generic reconstruction;
 wherein the loss function includes one or more fourth terms that encourage a corresponding specified proper subset of the set of features defined by the embedded representation of the generic reconstruction and the specified proper subset of the set of features defined by the embedded representation of the negative biometric data sample to be less similar and that encourage the specified proper subset of the set of features defined by the embedded representation of the generic reconstruction and the specified proper subset of the set of features defined by the embedded representation of the positive biometric data sample to be more similar.

20. The non-transitory computer storage media of claim 19, wherein determining a generic embedded representation from the embedded representation of the positive biometric data sample comprises:
 determining a first proper subset of the set of features defined by the generic embedded representation by averaging the specified proper subset of the set of features defined by the embedded representation of the positive biometric data sample and corresponding specified proper subsets of sets of features defined by embedded representations of one or more additional positive biometric data samples.

* * * * *